(12) United States Patent
Jeon et al.

(10) Patent No.: US 7,266,402 B2
(45) Date of Patent: Sep. 4, 2007

(54) APPARATUS AND METHOD FOR DETERMINING BLOOD SUGAR LEVEL WITHOUT BLOOD USING DARK ADAPTATION OF OPTIC NERVE, AND COMPUTER READABLE RECORDING MEDIUM STORING COMPUTER PROGRAM PERFORMING THE METHOD

(75) Inventors: Kye-jin Jeon, Suwon-si (KR); Ji-deog Kim, Seoul (KR); In-duk Hwang, Suwon-si (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 11/311,381

(22) Filed: Dec. 20, 2005

(65) Prior Publication Data

US 2006/0167352 A1   Jul. 27, 2006

(30) Foreign Application Priority Data

Jan. 26, 2005   (KR) .................... 10-2005-0007239

(51) Int. Cl.
*A61B 5/00*   (2006.01)

(52) U.S. Cl. ...................................... 600/319; 600/318
(58) Field of Classification Search ................ 600/316, 600/318, 319, 320, 322
See application file for complete search history.

(56) References Cited

U.S. PATENT DOCUMENTS

| | | | |
|---|---|---|---|
| 3,936,162 A | 2/1976 | Krakau et al. | |
| 2004/0138539 A1* | 7/2004 | Jay et al. ..................... | 600/322 |
| 2005/0010091 A1* | 1/2005 | Woods et al. ................ | 600/316 |

FOREIGN PATENT DOCUMENTS

KR   2000-0010539 A   2/2000

* cited by examiner

*Primary Examiner*—Eric Winakur
*Assistant Examiner*—Etsub Berhanu
(74) *Attorney, Agent, or Firm*—Sughrue Mion, PLLC

(57) ABSTRACT

Provided are an apparatus and a method for determining blood sugar level without blood using dark adaptation of the optic nerve, and a computer-readable recording medium storing a computer program performing the method. The apparatus irradiates stimulating light onto the pupil of a subject. A detecting device determines when the subject responds to the light. A calculator then calculates the blood sugar based on the response to the stimulating light.

24 Claims, 5 Drawing Sheets

APPARATUS AND METHOD FOR DETERMINING BLOOD SUGAR LEVEL WITHOUT BLOOD USING DARK ADAPTATION OF OPTIC NERVE, AND COMPUTER READABLE RECORDING MEDIUM STORING COMPUTER PROGRAM PERFORMING THE METHOD

BACKGROUND OF THE INVENTION

This application claims the benefit of Korean Patent Application No. 10-2005-0007239, filed on Jan. 26, 2005, in the Korean Intellectual Property Office, the disclosure of which is incorporated herein in its entirety by reference.

1. Field of the Invention

The present invention relates to the determination of blood sugar level, and more particularly, to an apparatus and a method for determining blood sugar level without blood using dark adaptation of the optic nerve, based on the fact that the threshold intensity with respect to time correlates with blood sugar level under a condition of blockage of external light, and a computer readable recording medium storing a computer program performing the method.

2. Description of the Related Art

A conventional apparatus for determining blood sugar level draws blood to make its measurement. Although an ordinary person can easily use the apparatus in their home, it is troublesome to draw blood for every measurement, and to sterilize the apparatus to prevent infection. In addition, the conventional apparatus for determining blood sugar level is unsanitary in its use of a needle for drawing blood.

To solve these problems, a technology of determining blood sugar level without blood has been proposed, using the fact that the threshold intensity over time correlates with the blood sugar level under a condition of blockage of external light. The threshold intensity is the lowest intensity of light required to recognize an object under a condition of blockage of external light, as a function of time. Here, the intensity of light refers to the intensity of light incident from the object to the pupil.

However, the conventional technology can obtain the threshold intensity only after a long time under a condition of blockage of external light.

In addition, since a subject determines the threshold intensity by their own sensing, the accuracy of the results cannot be assured, and thus the calculated blood sugar level may be inaccurate.

SUMMARY OF THE INVENTION

The present invention provides an apparatus for determining blood sugar level without blood using dark adaptation of the optic nerve by rapidly and accurately measuring a threshold intensity and an irradiation time and using the fact that the threshold intensity over time correlates with the blood sugar level under a condition of blockage of external light.

The present invention also provides a method of determining blood sugar level without blood using dark adaptation of the optic nerve by rapidly and accurately measuring a threshold intensity and an irradiation time and using the fact that the threshold intensity over time correlates with the blood sugar level under a condition of blockage of external light.

The present invention also provides a computer-readable recording medium storing a computer program for determining blood sugar level without blood by rapidly and accurately measuring a threshold intensity and an irradiation time and using the fact that the threshold intensity over time correlates with the blood sugar level under a condition of blockage of external light.

According to an aspect of the present invention, there is provided an apparatus for determining blood sugar level without blood using dark adaptation of the optic nerve, including: a controller which generates a control signal for controlling light which is irradiated onto the pupil of a subject; a light irradiator which responds to the control signal to irradiate a light onto the pupil shielded from external light while increasing an intensity of the light; a stimulus notifier which notifies the controller of an event that the subject recognizes the light; and a blood sugar level calculator which calculates the blood sugar level of the subject using a threshold intensity and an irradiation time according to the instruction of the controller, wherein the threshold intensity is the intensity of the light at the time of notification, the irradiation time is the time for which the light is irradiated onto the pupil, and the numerical values of the threshold intensity and the irradiation time are provided from the controller.

The light irradiator may include: a fixing light irradiator which irradiates a fixing light according to the control signal to fix the position of the pupil; and a variable light irradiator which stops the irradiation of the fixing light according to the control signal and irradiates the stimulating light onto the position irradiated with the fixing light while increasing the intensity of the stimulating light.

The fixing light irradiated by the fixing light irradiator may stimulate cone cells of the retina and the stimulating light irradiated by the variable light irradiator may stimulate rod cells of the retina.

The fixing light irradiated by the fixing light irradiator may be red light and the stimulating light irradiated by the variable light irradiator may be blue light.

The apparatus for determining blood sugar level may further include a focus tracer which traces the position of the pupil by irradiating an invisible focusing light onto the cornea according to the control signal and notifies the controller of the position of the traced pupil.

The stimulating light irradiated by the light irradiator may stimulate cone cells or rod cells of the retina.

The light irradiator may simultaneously irradiate light stimulating cone cells of the retina and light stimulating rod cells of the retina, as the stimulating light.

The stimulating light irradiated by the light irradiator may pass through the pupil to reach rod cells of the retina.

The stimulus notifier may be a user's operation unit which is pressed to notify the controller of an event that the subject recognizes the stimulating light.

The stimulus notifier may be an electroencephalogram (EEG) detector which detects the EEG of the subject and notifies the controller of an event that the subject recognizes the stimulating light.

The stimulus notifier may notify the controller of an event that the subject recognizes the stimulating light at the moment when an α-wave disappears from the detected EEG.

The light irradiator may respond to the control signal to irradiate an initialization light onto the pupil and irradiate the stimulating light onto the pupil blocked from external light while increasing the intensity of the stimulating light.

The apparatus for determining blood sugar level may further include a light sensor which senses the intensity of the stimulating light at the moment of notification to notify the controller.

The apparatus for determining blood sugar level may further include a display for displaying the calculated blood sugar level.

According to another aspect of the present invention, there is provided a method of determining blood sugar level without blood using dark adaptation of the optic nerve, including: irradiating a initialization light onto the pupil of a subject blocked from external light and stopping the irradiation; irradiating a stimulating light onto the pupil while increasing an intensity of the stimulating light; notifying that the subject has recognized the stimulating light; and being provided with the numerical value of a threshold intensity, which is the intensity of the stimulating light at the moment of notification, and the numerical value of an irradiation time, which is the time for which the stimulating light is irradiated onto the pupil, and calculating the blood sugar level of the subject using the threshold intensity and the irradiation time.

According to another aspect of the present invention, there is provided a computer-readable recording medium storing a computer program performing a method of determining blood sugar level without blood using dark adaptation of the optic nerve, including: irradiating a initialization light onto the pupil of a subject blocked from external light and stopping the irradiation; irradiating a stimulating light onto the pupil while increasing an intensity of the stimulating light; notifying when the subject recognizes the stimulating light; and being provided with the numerical value of a threshold intensity, which is the intensity of the stimulating light at the moment of notification, and the numerical value of an irradiation time which is the time for which the stimulating light is irradiated onto the pupil, and calculating the blood sugar level of the subject using the threshold intensity and the irradiation time.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF EXEMPLARY EMBODIMENTS

The present invention will now be described more fully with reference to the accompanying drawings, in which exemplary embodiments of the invention are shown. It is to be understood that the terminology used herein is for the purpose of describing particular embodiments only, and is not intended to be limiting, since the scope of the present invention will be limited only by the appended claims.

Figure 1:
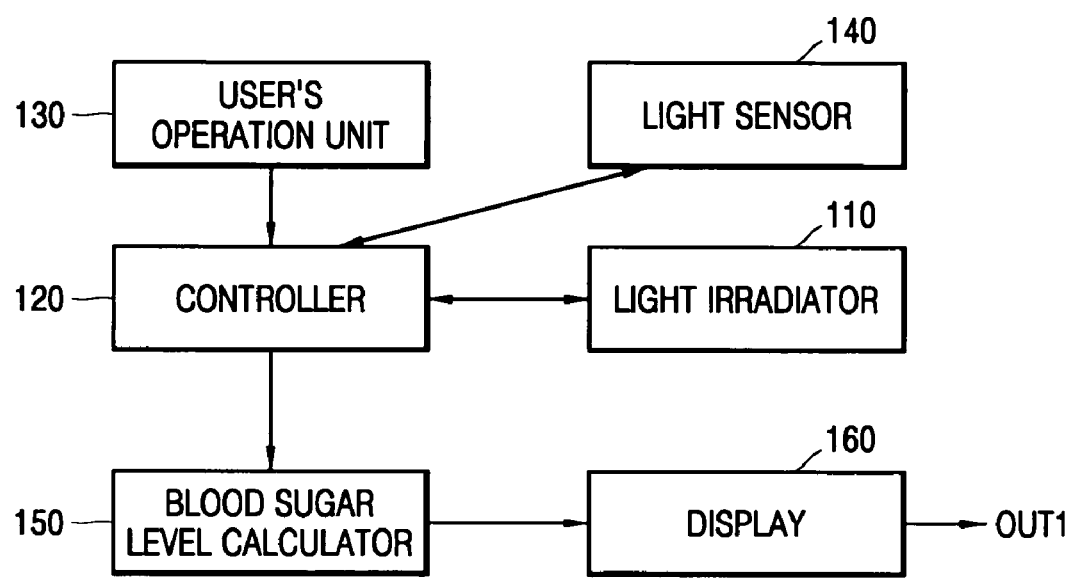
FIG. 1 is a block diagram for explaining an apparatus for determining blood sugar level without blood using dark adaptation of the optic nerve according to an embodiment of the present invention.

FIG. 1 is a block diagram for explaining an apparatus for determining blood sugar level without blood using dark adaptation of the optic nerve according to an embodiment of the present invention. The apparatus for determining blood sugar level includes a light irradiator 110, a controller 120, a stimulus notifier 130, a light sensor 140, a blood sugar level calculator 150 and a display 160.

The light irradiator 110 irradiates light onto the pupil 230 (see FIG. 2) of a subject blocked from external light, while increasing the intensity. Hereinafter, this light is referred to as "a stimulating light" or "a rod cell stimulating light". The light irradiator 110 can also irradiate an initialization light, a fixing light and a focusing light.

The controller 120 generates control signals for controlling the operation of the light irradiator 110, the light sensor 140 and the blood sugar calculator 150. In particular, the controller 120 controls the operation of the light irradiator 110 to control light irradiated onto the pupil 230 of the subject.

It is preferable that only light from the light irradiator 110 is allowed to reach the pupil 230 of the subject. That is, external light may be blocked. An eye bandage may be put over the subject's eyes to achieve this. At this time, the light irradiator 110 irradiates light inside the eye bandage onto the pupil 230.

External light can also be blocked by entering a dark room. However, to miniaturize the apparatus for determining blood sugar level, it is preferable to use the eye bandage. This produces the same results as when the subject enters a dark room.

Once all external light, such as sunlight or incandescent light, is blocked by the eye bandage, the optic nerve of the subject undergoes dark adaptation. The dark adaptation is also called adaptation to darkness, and is the mechanism which allows human vision to function under a very wide range of illumination levels.

When an x axis denotes an irradiation time and a y axis denotes a threshold intensity, a curve can be obtained where the threshold intensity is in inverse proportion to the irradiation time (hereinafter, called "a dark adaptation curve").

The threshold intensity is a function of the irradiation time, and is the lowest intensity required to recognize an incident light each time. Alternatively, the threshold intensity may be a function of the time taken for the pupil 230 to adapt to darkness after external light is blocked.

The irradiation time is the total time for which light is irradiated onto the pupil 230 shielded from external light.

In general, when the irradiation time is about 7 min, a bending point appears in the dark adaptation curve. This is called "Kohlrausch's kink". While cone cells of the retina initially act to increase sensitivity by 10 times, the sensitivity of rod cells increases and replaces the cone cells as the dark adaptation proceeds. That is, owing to the adaptation of rod cells, their sensitivity eventually increases by about 1000 times. While it takes 45 minutes to complete the dark adaptation, it takes only about 1 to 2 minutes to readjust when going out from a dark place to a light place.

It is already known in the medical field that the dark adaptation curve is associated with the blood sugar level of a subject. That is, the higher the blood sugar level, the faster the threshold intensity decreases.

Thus, if only the threshold intensity and the irradiation time are acquired, the blood sugar level of a subject can be calculated. However, it is difficult to wait until the completion of the dark adaptation in order to acquire the threshold intensity and the irradiation time, because the subject must be under the inconvenient examination conditions for a long time.

The present invention provides a technique for rapidly obtaining accurate numerical values of the threshold intensity and the irradiation time by irradiating the stimulating light onto the pupil 230 while gradually increasing the intensity, and accurately determining the moment when the subject recognizes the irradiated stimulating light.

The light irradiator 110 irradiates the stimulating light under the control of the controller 120 as described above, and the stimulating light may be incident on rod cells 242 of visual cells 240 of the retina through the pupil 230. Meanwhile, light of a smaller wavelength more easily stimulates the rod cells 242. For example, blue light stimulates the rod cells 242 more easily than red light.

Figure 2:
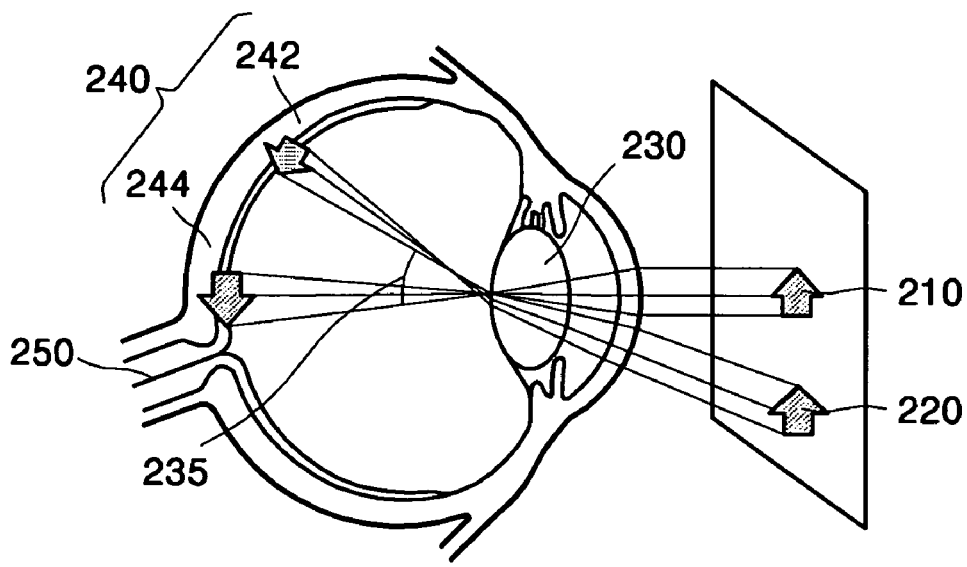
FIG. 2 is a reference diagram for explaining a fixing light and a stimulating light irradiated onto the pupil.

To ensure that the stimulating light is incident on the rod cells 242 of the visual cells 240 of the retina, the light irradiator 110 may include a fixing light irradiator (not shown) and a variable light irradiator (not shown). FIG. 2 is a reference diagram for explaining the fixing light and the stimulating light irradiated onto the pupil 230. The fixing light irradiator irradiates the fixing light 210 according to a control signal from the controller 120 to fix the position of the pupil 230. Since the fixing light 210 irradiated onto the pupil 230 is generally incident on cone cells 244 of visual cells 240 of the retina, red light which easily stimulates the cone cells 244 may be used as the fixing light 210. Meanwhile, the variable light irradiator stops irradiating the fixing light 210 and irradiates the stimulating light 220 onto the position on the pupil irradiated with the fixing light 210, while increasing the intensity of the stimulating light 220, according to a control signal from the controller 120. The irradiation may be performed such that the stimulating light 220 passes through the position irradiated with the fixing light 210, and reaches the rod cells 242, while increasing the intensity of the stimulating light.

There may be no gap of time between stopping the irradiation of the fixing light 210 and beginning the irradiation of the stimulating light 220. This is because the subject moves the eyeball during any time gap, thus changing the position of the pupil 230, which causes the variable light irradiator to irradiate the stimulating light 220 onto the wrong position.

The variable light irradiator maintains an angle 235 between the path of the stimulating light 220 and the path of the fixing light 210 irradiated by the fixing light irradiator. The fixing light 210 is generally incident on cone cells 244, whereas the stimulating light 220 may be incident on rod cells 242. Cone cells 244 of the visual cells 240 of the retina are usually distributed at the circumference of yellow spots (not shown), and rod cells 242 are usually distributed across the remaining portion of the retina except for the circumference of the yellow spots. In consideration of the spatial distribution of the visual cells 240 of the retina, the angle 235 may be 12 to 20 degrees.

An image 250 formed on the visual cells 240 of the retina is recognized by the cerebrum through an optic nerve 250.

The intensity of the stimulating light 220 irradiated by the variable light irradiator of the light irradiator 110 onto the rod cells 242 gradually increases. In this case, the irradiation time increases and the threshold intensity decreases gradually. Meanwhile, the intensity of the stimulating light 220 irradiated onto the rod cells 242 gradually increases. Thus, the subject recognizes that the stimulating light 220 has irradiated when the intensity of the stimulating light reaches the threshold intensity.

At this moment, the stimulus notifier 130 informs the controller 120 of the fact that the subject has recognized the stimulating light 220. The stimulus notifier 130 may be a user's operation unit 130 which is operated to notify the controller 120 of the recognition. For example, the user's operation unit 130 can be a button which the subject can press to notify the controller 120 of an event that the subject recognizes the stimulating light 220.

The controller 120 provides the blood sugar level calculator 150 with the numerical values of the threshold intensity and the irradiation time as soon as it is notified, and requests the calculation of the subject's blood sugar level using the provided numerical values. The blood sugar level calculator 150 calculates the blood sugar level of the subject based on the medical common sense that the threshold intensity with the passage of time under a condition of blockage of external light correlates with blood sugar level.

At this time, the controller 120 can provide the blood sugar level calculator 150 with the intensity of the stimulating light 220 irradiated by the light irradiator 110 when the stimulus notifier 130 informs the controller 120 of the recognition fact as the threshold intensity. Since the controller 120 instructs the light irradiator 110 to irradiate the stimulating light 220, it always recognizes the intensity of the stimulating light 220. Similarly, the controller 120 also provides the blood sugar level calculator 150 with the numerical value of the irradiation time when the stimulus notifier 130 informs the controller 120 of the recognition fact.

Meanwhile, the controller 120 can directly sense the intensity of the stimulating light 220 irradiated by the light irradiator 110 in order to obtain the numerical value of the threshold intensity. In this case, a light sensor 140 is further included. The light sensor 140 may operate according to a control signal from the controller 120 generated when the stimulus notifier 130 informs the controller 120 of the recognition.

The display 160 displays the numerical value of the blood sugar level calculated by the blood sugar level calculator 150. "OUT 1" denotes the numerical value of the blood sugar level displayed.

Figure 3:
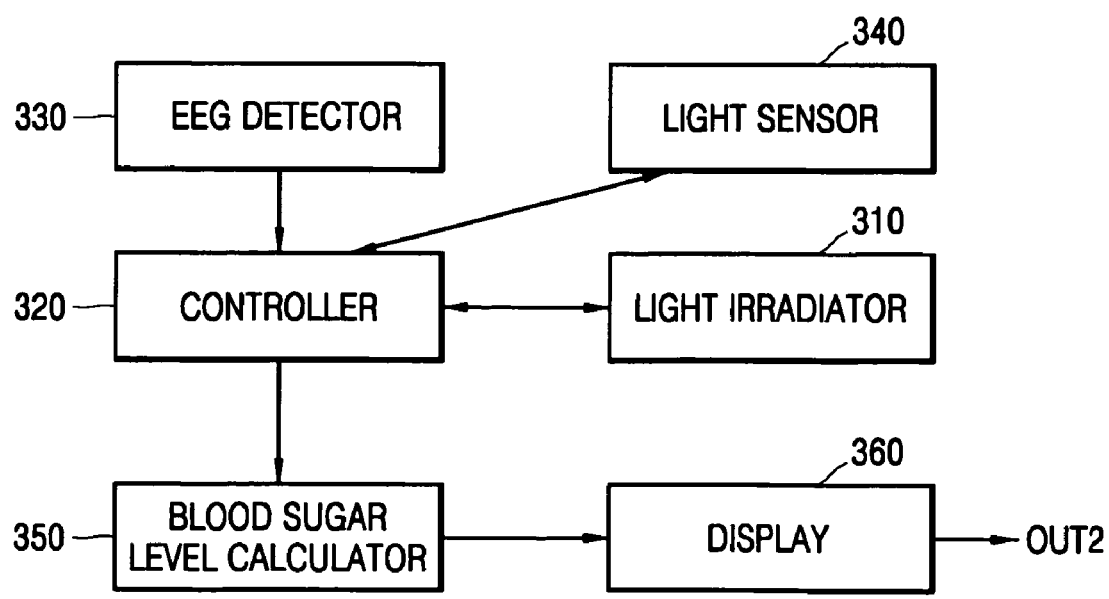
FIG. 3 is a block diagram for explaining an apparatus for determining blood sugar level without blood using dark adaptation of the optic nerve according to another embodiment of the present invention.

FIG. 3 is a block diagram for explaining an apparatus for determining blood sugar level without blood using dark adaptation of the optic nerve according to another embodiment of the present invention. The apparatus includes a light irradiator 310, a controller 320, a stimulus notifier 330, a light sensor 340, a blood sugar level calculator 350 and a display 360.

The elements 310, 320, 340, 350 and 360 are the same as the elements 110, 120, 140, 150 and 160 illustrated in FIG. 1, and thus their descriptions will not be repeated. Here, "OUT 2" denotes the numerical value of the blood sugar level displayed.

The stimulus notifier 330 may be an electroencephalogram (EEG) detector which detects the EEG of the subject and notifies the controller 320 when the subject recognizes the stimulating light 220 irradiated onto the pupil 230.

The EEG represents the electrical activity of cortical neurons detected on the surface of the subject's scalp. The EEG generally has a frequency of about 1 to 50 Hz and a potential of 20 to 200.

In particular, the EEG includes an α-wave with a frequency of 8 to 13 Hz, a β-wave with a frequency of 18 to 30 Hz, a δ-wave with a frequency of 0.5 to 4 Hz, and a θ-wave with a frequency of 4 to 7 Hz.

In the EEG detected when it becomes opening eyes in a stable state with closing eyes, the α-wave disappears at once and the β-wave appears, which is called "α-blocking". That is, the β-wave is detected when a predetermined signal is transmitted to the optic nerve 250, and this principle can be used by the stimulus notifier 330. When irradiating only the stimulating light 220 onto the pupil 230 with increasing the intensity under a condition of blockage of external light, the α-wave is not detected for a moment. This is the time when the subject recognizes the stimulating light 220 incident on the pupil 230. In this way, the stimulus notifier 330 notifies the controller 320 of the recognition. Since the stimulus notifier 330 accurately catches without error the moment when the subject recognizes the stimulating light 220, it ensures a higher accuracy of the blood sugar level than the user's operation unit 130.

The light irradiator 110 or 310 may respond to the control signal to irradiate a predetermined amount of an initialization light (not shown) onto the pupil 230 and irradiate the stimulating light 220 onto the pupil 230 blocked from external light while increasing the intensity. That is, the light irradiator 110 or 310 may initialize the state of the pupil 230 by irradiating the initialization light, before irradiating the fixing light 210 or the stimulating light 220. In this case, the light irradiator 110 or 310 may irradiate the fixing light 210 or the stimulating light 220 onto the pupil 230 after irradiating a predetermined amount of an initialization light.

Figure 4:
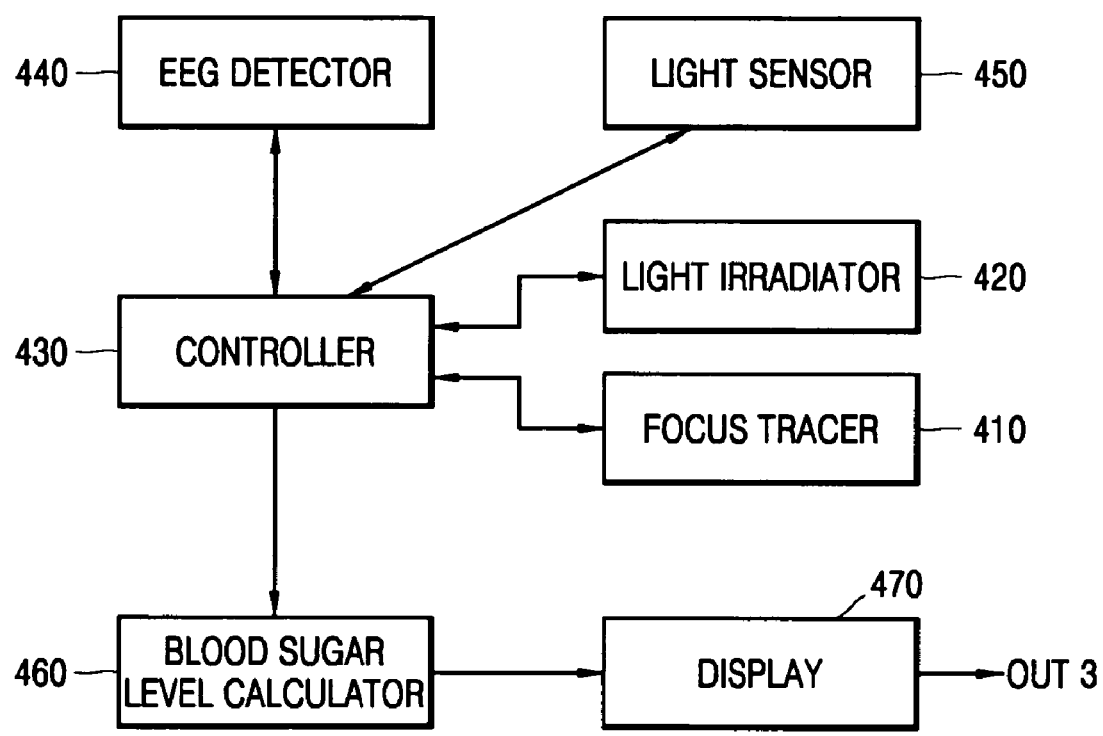
FIG. 4 is a block diagram for explaining an apparatus for determining blood sugar level without blood using dark adaptation of the optic nerve according to another embodiment of the present invention.

FIG. 4 is a block diagram for explaining an apparatus for determining blood sugar level without blood using dark adaptation of the optic nerve according to another embodiment of the present invention. The apparatus includes a focus tracer 410, a light irradiator 420, a controller 430, a stimulus notifier 440, a light sensor 450, a blood sugar level calculator 460 and a display 470.

The elements 420, 430, 440, 450, 460 and 470 are the same as the elements 110, 120, 130, 140, 150 and 160 illustrated in FIG. 1, and thus their descriptions will not be repeated. Here, "OUT 3" denotes the numerical value of the blood sugar level displayed.

The focus tracer 410 traces the position of the pupil 230 by irradiating an invisible focusing light (not shown) onto the cornea according to a control signal from the controller 430, and informs the controller 430 of the position of the pupil 230. This determines the position of the pupil 230 in order to accurately irradiate the initialization light, the fixing light 210 and the stimulating light 220 onto the pupil 230. Meanwhile, the focusing light may be infrared. In this case, the stimulating light 220 may stimulate either the cone cells 244 or the rod cells 242 of the visible cells 240 of the retina. Alternatively, the light irradiator 420 can simultaneously irradiate light to stimulate the cone cells 244 and light to stimulate the rod cells 242.

Figure 5:
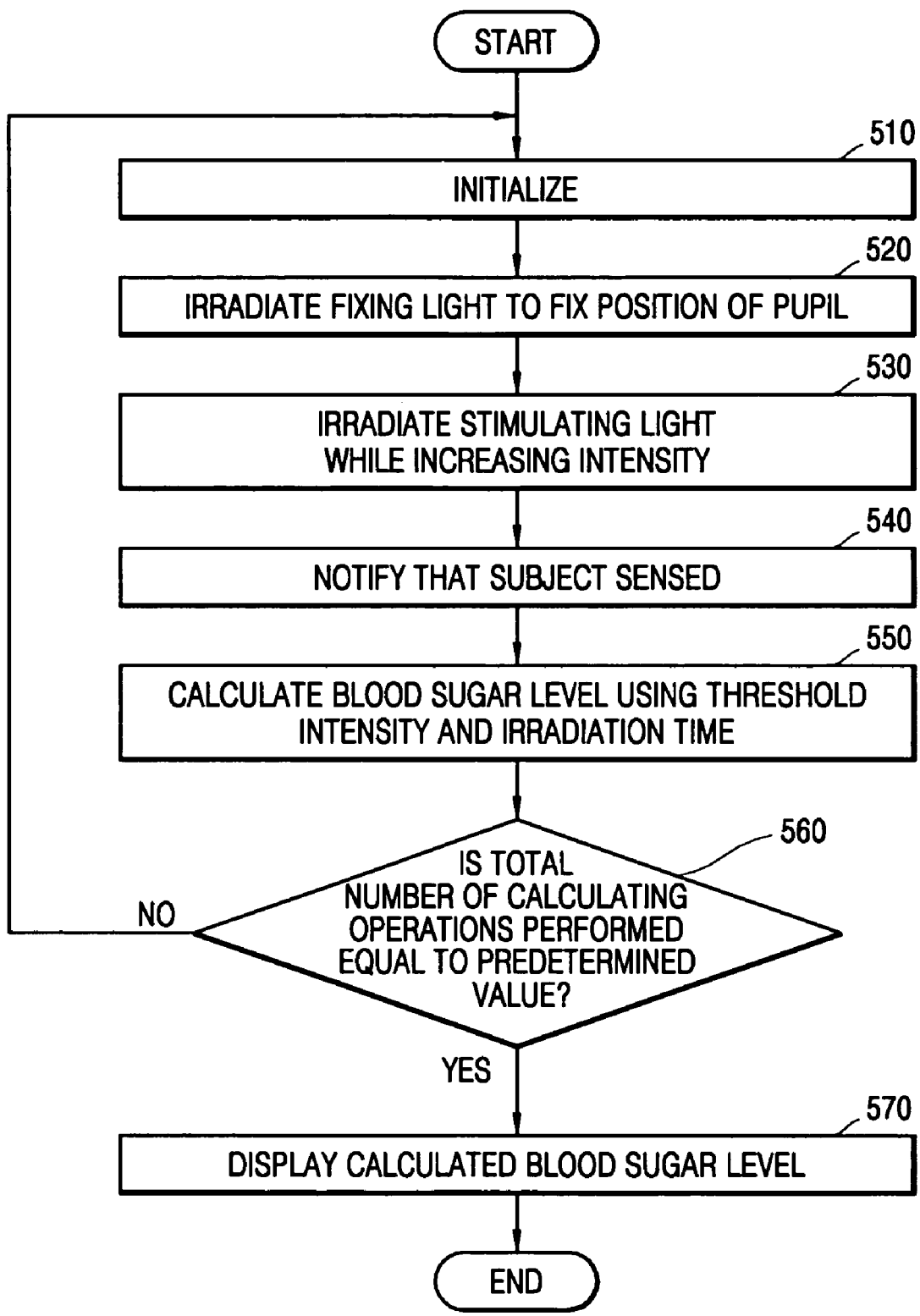
FIG. 5 is a flow chart for explaining a method of determining blood sugar level without blood using dark adaptation of the optic nerve according to an embodiment of the present invention.

FIG. 5 is a flow chart for explaining a method of determining blood sugar level without blood using dark adaptation of the optic nerve according to an embodiment of the present invention. The method includes calculating blood sugar level by irradiating a light to obtain the numerical values of a threshold intensity and irradiation time (operations 510 to 550) and displaying the result (operations 560 to 570).

The light irradiator 110 or 310 irradiates the initialization light onto the pupil 230 to initialize the amount of light incident on the pupil 230 (operation 510). The light irradiator 110 or 310 irradiates the fixing light 210 onto the pupil 230 to fix the position of the pupil 230 (operation 520), and irradiate the stimulating light 220 at an increasing intensity (operation 530).

At the moment of recognition, the stimulus notifier 130 or 330 informs the controller 120 or 320 of the recognition, provide the blood sugar level calculator 150 or 350 with the numerical values of the threshold intensity and the irradiation time, and request the calculation of the blood sugar level. Thereby, the blood sugar level calculator 150 or 350 calculates the blood sugar level (operation 550).

At this time, the controller 120 or 320 decides whether the total number of calculating operations performed is equal to a predetermined value (operation 560). and if the result is less than the predetermined value, the operation 510 is performed again.

However, if the total number of calculating operations performed is equal to the predetermined value, the display 160 or 360 displays the blood sugar level (operation 570). How many times the calculating operation is performed is established in advance.

Figure 6:
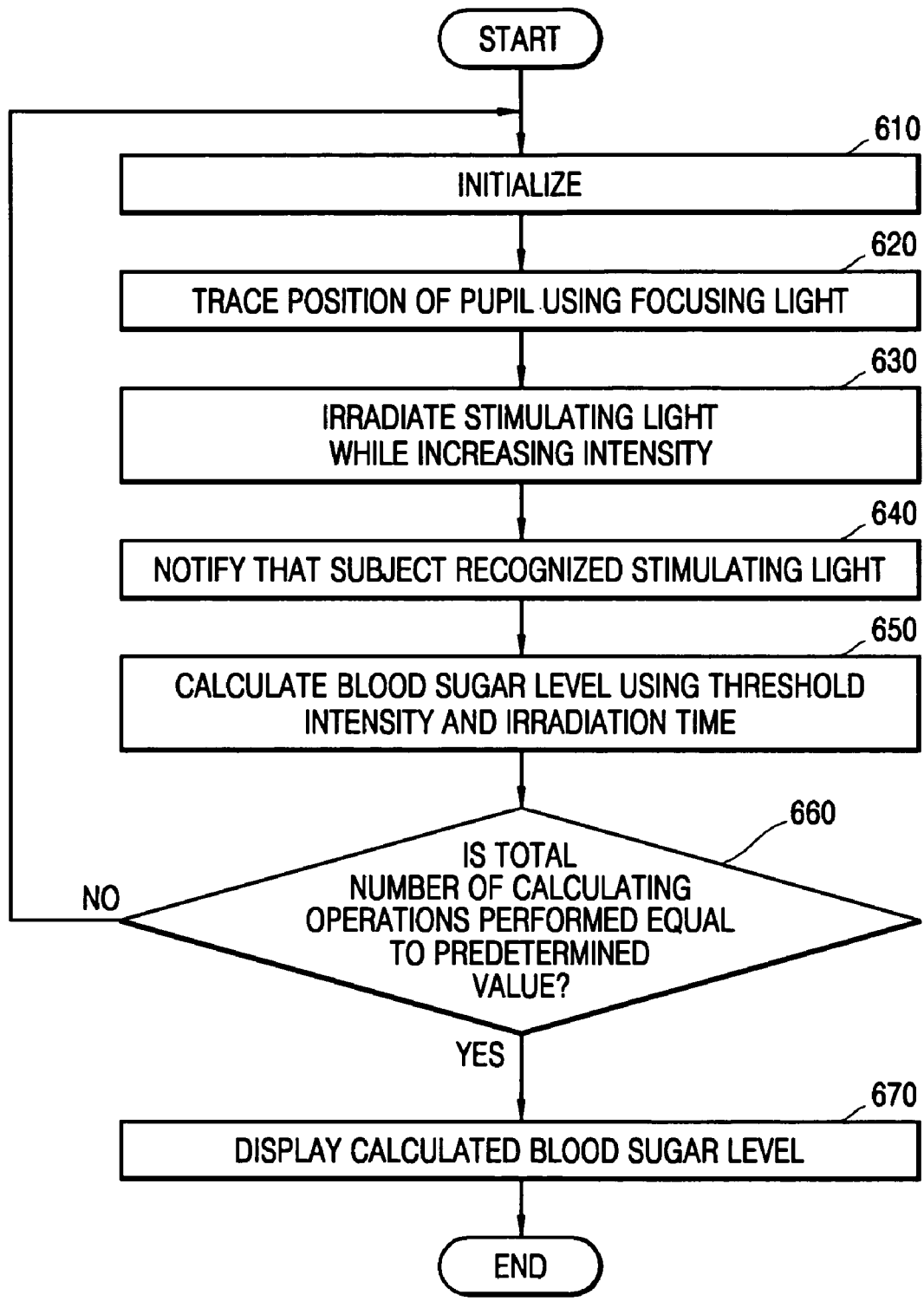
FIG. 6 is a flow chart for explaining a method of determining blood sugar without blood using dark adaptation of the optic nerve according to another embodiment of the present invention.

FIG. 6 is a flow chart for explaining a method of determining blood sugar level without blood using dark adaptation of the optic nerve according to another embodiment of the present invention. The method includes calculating blood sugar level by irradiating a light to obtain numerical values of a threshold intensity and irradiation time (operations 610 to 650) and displaying the result (operations 660 to 670).

The elements 510 and 530 to 570 are the same as the elements 610 and 630 to 670 in FIG. 5, and thus their descriptions will not be repeated.

The focus tracer 410 traces the position of the pupil 230 by irradiating the focusing light onto the pupil 230 (operation 620). Thus, the position of the pupil 230 can always be determined.

These exemplary embodiments use an initialization light, a fixing light, a focusing light and a stimulating light in various combinations, however, the present invention is not limited to the combinations described in these exemplary embodiments, and any combination or number of the aforementioned type of lights may be used to implement the invention.

The present invention can also be implemented as computer-readable code stored on a computer-readable recording medium. The computer-readable recording medium includes all kinds of recording medium which store data that can be read by a computer system. Examples of such a recording medium include ROM, RAM, CD-ROM, magnetic tape, floppy disc, optical data storage, and the like. In addition, the recording medium may be implemented in the form of a carrier wave (for example, transmission through the internet). The computer-readable recording medium can also be distributed over network coupled computer systems so that the computer-readable code is stored and executed in a distributed fashion. Functional programs, code and code segments for implementing the present invention can easily be conceived by programmers in the art.

As described above, the apparatus and the method for determining blood sugar level without blood using dark adaptation of the optic nerve, and the recording medium storing a computer program performing the method, according to embodiments of the present invention can rapidly and accurately calculate the threshold intensity and the irradiation time, to rapidly and accurately determine a subject's blood sugar level, based on the fact that the threshold intensity over time is associated with the numerical value of the blood sugar level under the condition where external light is blocked.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An apparatus for determining blood sugar level without blood using dark adaptation of the optic nerve, comprising:
a controller which generates a control signal for controlling light which is irradiated onto a pupil of a subject;
a light irradiator which responds to the control signal to irradiate a stimulating light onto the pupil;
a stimulus notifier which notifies the controller at a time that the subject has a predetermined response to the stimulating light; and
a blood sugar level calculator which calculates the blood sugar level of the subject using a threshold intensity and an irradiation time according to an instruction from the controller,
wherein an intensity of the stimulating light changes over a duration of time and the threshold intensity is the intensity of the stimulating light at the time of notification, and the irradiation time is the duration of time for which the stimulating light is irradiated onto the pupil before notification.

2. The apparatus of claim 1, wherein the light irradiator further comprises:
a fixing light irradiator which irradiates a fixing light at a position on the pupil according to the control signal in order to fix the pupil; and
a variable light irradiator which irradiates the stimulating light directed at a substantially same position on the pupil where the fixing light is irradiated.

3. The apparatus of claim 2, wherein the fixing light irradiated by the fixing light irradiator stimulates cone cells of the retina for a first time period and the stimulating light irradiated by the variable light irradiator stimulates rod cells of the retina following the first time period.

4. The apparatus of claim 3, wherein the fixing light irradiated by the fixing light irradiator is red light and the stimulating light irradiated by the variable light irradiator is blue light, and external light is substantially blocked from entering the pupil.

5. The apparatus of claim 2, further comprising a focus light irradiator which irradiates a focusing light to identify a pupil position, wherein the pupil position is provided to the controller, and the fixing light irradiator and the stimulating light irradiator are directed to the position on the pupil based on the pupil position.

6. The apparatus of claim 5, wherein the stimulating light irradiated by the variable light irradiator is directed to the rod cells of the retina.

7. The apparatus of claim 5, wherein the fixing light irradiated by the fixing light irradiator is directed to the cone cells of the retina.

8. The apparatus of claim 5, wherein the variable light irradiator simultaneously irradiates light stimulating cone cells of the retina and rod cells of the retina.

9. The apparatus of claim 5, further comprising an initialization light irradiator which irradiates an initializing light,
wherein the focusing light is irradiated to determine the pupil position, the initializing light is then irradiated for a predetermined amount of time, the fixing light is irradiated after the predetermined amount of time and after the pupil is fixed by the fixing light, and the stimulating light is irradiated after the position of the pupil is fixed.

10. The apparatus according to claim 2, wherein the fixing light is directed on a first path and the stimulating light is directed on a second path toward the substantially same position on the pupil with an angle of 12 to 20 degrees between the first path and second path.

11. The apparatus of claim 1, wherein the stimulus notifier is a user's operation unit activated by the user.

12. The apparatus of claim 1, wherein the stimulus notifier is an electroencephalogram detector which detects the electroencephalogram of the subject.

13. The apparatus of claim 12, wherein the predetermined response of the subject is indicated when an $\alpha$-wave disappears from the detected electroencephalogram.

14. The apparatus of claim 1, further comprising an initialization light irradiator for irradiating an initialization light onto the pupil for a predetermined time,
wherein said stimulating light is irradiated after the predetermined time.

15. The apparatus of claim 1, further comprising a light sensor which senses the intensity of the stimulating light at the moment of notification, to notify the controller.

16. The apparatus of claim 1, further comprising a display for displaying the calculated blood sugar level.

17. A method of determining blood sugar level without blood using dark adaptation of the optic nerve, comprising:
irradiating a stimulating light onto a pupil of a subject substantially blocked from external light, while increasing an intensity of the stimulating light;
notifying that the subject has responded to the stimulating light;
providing a calculated blood sugar level based on the intensity of the stimulating light at the moment of notification, and the time for which the stimulating light is irradiated onto the pupil; and
irradiating a focusing light onto a cornea to determine a position of the pupil, wherein the stimulating light is irradiated based on the position determined.

18. The method of claim 17, wherein the stimulating light passes through the pupil to reach rod cells of the retina.

19. The method of claim 17, further comprising:
irradiating a fixing light to fix the position of the pupil, wherein the irradiating of the fixing light is stopped prior to irradiating the stimulating light.

20. The method of claim 17, further comprising:
irradiating an initialization light for a predetermined period of time, wherein the stimulating light is irradiated after the predetermined period of time of irradiating the initialization light.

21. The method of claim 20, wherein the stimulating light is irradiated immediately after the predetermined period of time of irradiating the initialization light.

22. The method of claim 17, further comprising displaying the calculated blood sugar level.

23. The method of claim 16, further comprising:
irradiating an initialization light for a predetermined period of time directed by the determined pupil position; and irradiating a fixing light to fix the position of the pupil,
wherein the focusing light is irradiated first to determine the position of the pupil, the initialization light is irradiated second for a predetermined period of time, the fixing light is irradiated after the predetermined time and the stimulating light is irradiated after the position of the pupil is fixed.

24. A computer-readable recording medium storing a computer program performing a method of determining blood sugar level without blood using dark adaptation of the optic nerve, comprising:

irradiating an initialization light onto the pupil of a subject blocked from external light and stopping the irradiation;

irradiating a stimulating light onto the pupil while increasing an intensity of the stimulating light;

notifying when the subject recognizes the stimulating light;

being provided with the numerical value of a threshold intensity, which is the intensity of the stimulating light at the moment of notification, and the numerical value of an irradiation time which is the time for which the stimulating light is irradiated onto the pupil, and calculating the blood sugar level of the subject using the threshold intensity and the irradiation time; and irradiating a focusing tight onto a cornea to determine a position of the pupil, wherein the stimulated light is irradiated based on the position determined.

* * * * *